United States Patent [19]

Farge et al.

[11] 4,287,197

[45] Sep. 1, 1981

[54] ANTIVIRAL ISOQUINOLINE DERIVATIVES

[75] Inventors: Daniel Farge, Thiais; Alain Jossin, St-Cloud; Gerard Ponsinet, Sucy-en-Brie; Daniel Reisdorf, Thiais, all of France

[73] Assignee: Rhone-Poulenc Industries, Paris, France

[21] Appl. No.: 147,248

[22] Filed: May 6, 1980

[30] Foreign Application Priority Data

May 9, 1979 [FR] France ............................. 79 11707
Dec. 4, 1979 [FR] France ............................. 79 29752

[51] Int. Cl.³ .................... A61K 31/47; C07D 513/04
[52] U.S. Cl. ..................................... 424/258; 546/80; 546/139; 546/140; 546/143; 546/150
[58] Field of Search ........................... 546/80; 424/258

[56] References Cited

U.S. PATENT DOCUMENTS 4,064,247  12/1977  Farge et al. ....................... 546/80 X
4,108,999   8/1978  Farge et al. ....................... 546/80 X
4,153,698   5/1979  Farge et al. ....................... 546/80 X Primary Examiner—Richard A. Schwartz
Attorney, Agent, or Firm—Stevens, Davis, Miller & Mosher

[57] ABSTRACT

Isoquinoline derivatives of the formula:

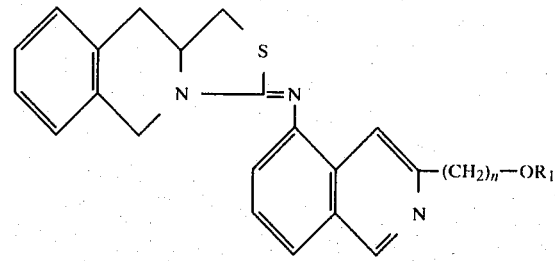

wherein $R_1$ represents alkyl of 1 through 8 carbon atoms, and n represents 1 or 2, are new compounds possessing useful pharmacological properties. They are particularly valuable as analgesic, anti-inflammatory, antipyretic or antiviral agents.

7 Claims, No Drawings

ANTIVIRAL ISOQUINOLINE DERIVATIVES

DESCRIPTION

This invention relates to new therapeutically useful isoquinoline derivatives, to processes for their preparation and to pharmaceutical compositions containing them.

In the specification of our U.S. Pat. No. 4,153,698 (granted May 8, 1979) we have described and claimed isoquinoline derivatives of the general formula:

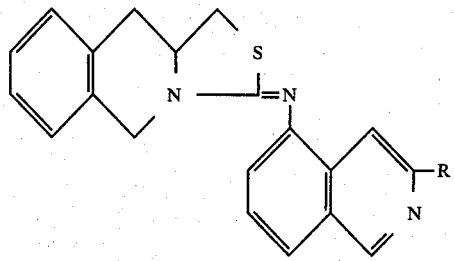
I wherein R represents an alkyl radical containing from 1 to 10 carbon atoms, and non-toxic pharmaceutically acceptable acid addition salts thereof, which possess useful pharmacological properties and are, in particular, useful as anti-inflammatory, analgesic and antipyretic agents.

As a result of further research and experimentation it has now been found that related compounds wherein symbol R represents an alkoxyalkyl grouping of the general formula:

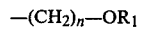
$-(CH_2)_n-OR_1$                II wherein $R_1$ represents a straight- or branched-chain alkyl radical containing 1 to 8 carbon atoms and n represents 1 or 2, also possess useful pharmacological properties.

The present invention accordingly provides new isoquinoline derivatives of the general formula:

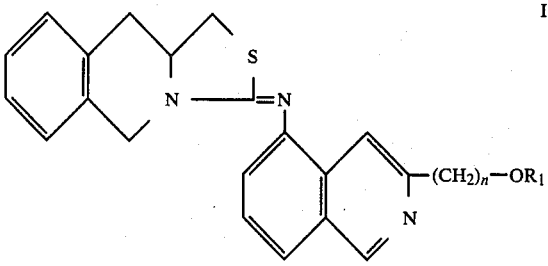
III wherein $R_1$ and n are as hereinbefore defined, and acid addition salts thereof.

The compounds of general formula III can exist in (R) and (S) forms and the invention includes both such forms and mixtures thereof.

The compounds of general formula III can be prepared by application of processes disclosed in our aforementioned patent.

Thus they can be prepared, according to a feature of the present invention, by the process which comprises the cyclisation of a 1,2,3,4-tetrahydroisoquinoline of the general formula:

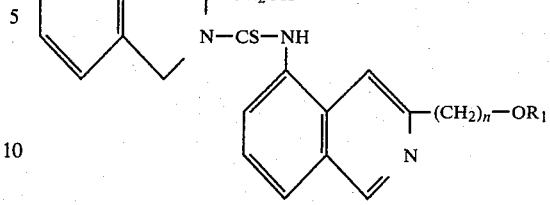
IV wherein $R_1$ and n are as hereinbefore defined.

The cyclisation is generally carried out by heating in an acid medium. Preferably the reaction is carried out at a temperature between 65° and 100° C. in an aqueous solution of an inorganic acid, e.g. in hydrochloric acid.

The 1,2,3,4-tetrahydroisoquinolines of general formula IV may be obtained by reacting an isothiocyanate of the general formula:

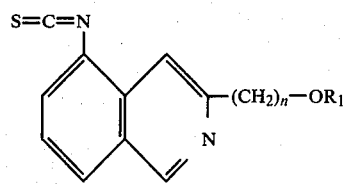
V (wherein $R_1$ and n are as hereinbefore defined) with 3-hydroxymethyl-1,2,3,4-tetrahydroisoquinoline of the formula:

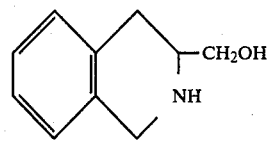
VI

The reaction is generally carried out in an organic solvent such as an alcohol, e.g. ethanol, at a temperature between 20° and 50° C.

3-Hydroxymethyl-1,2,3,4-tetrahydroisoquinoline can be prepared from phenylalanine in accordance with the method described by S. Yamada and T. Kunieda, Chem. Pharm. Bull., 15, 490 (1967).

When L-phenylalanine is used, the isoquinoline product of general formula III is obtained in the (S) form.

When D-phenylalanine is used, the isoquinoline product of general formula III is obtained in the (R) form.

When D,L-phenylalanine is used, the isoquinoline product of general formula III is obtained in the (RS) form.

The isothiocyanates of general formula V can be obtained by the reaction of carbon disulphide with a 5-aminoisoquinoline of the general formula:

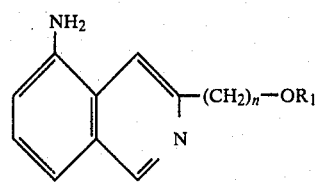
VII (wherein $R_1$ and n are as hereinbefore defined) followed by the addition of dicyclohexylcarbodiimide. The reaction is generally carried out in the presence of a base such as a tertiary amine, e.g. triethylamine. Advantageously it is effected in an organic solvent, such as pyridine, at a temperature between $-10°$ and $25°$ C.

The 5-aminoisoquinoline derivatives of general formula VII can be obtained from a 3-alkoxyalkylisoquinoline of the general formula:

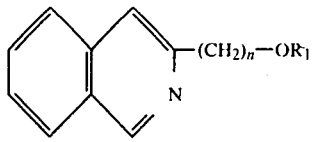
VIII (wherein $R_1$ and n are as hereinbefore defined) by applying the method of N. P. Buu-Hoï et al., J. Chem. Soc., 3924 (1964).

The isoquinoline derivatives of general formula VIII can be prepared by reacting an appropriate alkali metal alkoxide with a hydrohalide of a 3-halogenoalkylisoquinoline of the general formula:

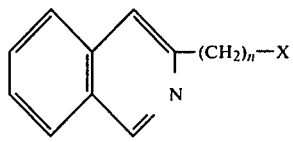
IX wherein n is as hereinbefore defined and X represents a chlorine or bromine atom. The reaction is generally carried out in solution in the corresponding alcohol $R_1OH$ (wherein $R_1$ is as hereinbefore defined) at a temperature between $20°$ C. and the reflux temperature of the reaction mixture.

The hydrohalides of the 3-halogenoalkylisoquinolines of general formula IX can be prepared by halogenating a 3-hydroxyalkylisoquinoline of the general formula:

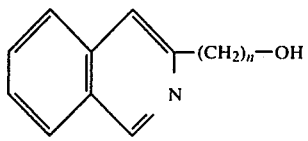
X wherein n is as hereinbefore defined.

Chlorination is generally carried out by the action of thionyl chloride at a temperature between $25°$ C. and the reflux temperature of the reaction mixture.

Bromination is generally carried out by the action of a concentrated aqueous solution of hydrobromic acid at a temperature between $50°$ C. and the reflux temperature of the reaction mixture.

3-Hydroxymethylisoquinoline can be prepared in accordance with the method described by B. R. Brown et al., J. Chem. Soc., 1145 (1951).

3-(2-Hydroxyethyl)isoquinoline can be prepared in accordance with the method described in Japanese Patent Publication 53/127483 (Derwent CPI 90295A).

The isoquinoline derivatives of general formula VIII wherein the symbol n represents 2 can also be obtained by hydrogenating an enol ether of the general formula:

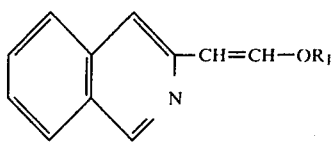
XI wherein $R_1$ is as hereinbefore defined. The hydrogenation is generally carried out in the presence of palladium-on-charcoal as catalyst in an organic solvent, such as an alcohol (e.g. methanol or ethanol), at a temperature of about $20°$ C. under a pressure of about 15 atmospheres.

The enol ethers of general formula XI can be prepared by means of a Wittig reaction by condensing a phosphorane of the general formula:

$$(C_6H_5)_3P\!=\!CH\!-\!OR_1 \qquad XII$$

(wherein $R_1$ is as hereinbefore defined) with 3-formylisoquinoline, under the conditions described by A. Maercker, Organic Reactions, 14, 270 (1965).

3-Formylisoquinoline can be obtained in accordance with the method described by J. Teague, J. Amer. Chem. Soc., 73, 688 (1951).

The phosphoranes of general formula XII can be prepared by treating the corresponding phosphonium bromide or chloride with a base, for example treatment with sodium methoxide in methanol or treatment with butyllithium in diethyl ether or tetrahydrofuran.

According to a further feature of the present invention, the isoquinoline derivatives of general formula III are prepared by the process which comprises reacting a 5-aminoisoquinoline of general formula VII (wherein $R_1$ and n are as hereinbefore defined) with a salt of the general formula:

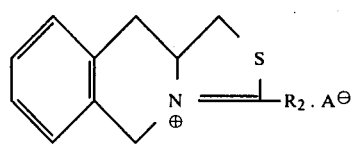
XIII wherein $R_2$ represents a chlorine atom, an alkylthio radical containing 1 to 4 carbon atoms (preferably methylthio), or a benzylthio radical, and $A^\ominus$ represents an anion.

When $R_2$ represents a chlorine atom, $A^\ominus$ represents a chloride ion. When $R_2$ represents an alkylthio or benzylthio radical, $A^\ominus$ represents an iodide, sulphate, tetrafluoroborate or fluorosulphonate ion.

When $R_2$ represents a chlorine atom and $A^\ominus$ represents a chloride ion, the reaction is preferably carried out in an organic solvent, such as acetonitrile, in the presence of a base, such as triethylamine, at a temperature of about $20°$ C.

When $R_2$ represents an alkylthio or benzylthio radical and $A^\ominus$ represents an iodide, sulphate, tetrafluoroborate or fluorosulphonate ion, the reaction is preferably carried out in a basic organic solvent, such as pyridine, at a temperature of about $20°$ C.

The salt of the general formula XIII wherein $R_2$ represents a chlorine atom and $A^\ominus$ represents a chloride ion can be obtained by the reaction of a chlorinating agent, such as phosgene, phosphorus pentachloride, thionyl chloride or oxalyl chloride, with 1,5,10,10a-tetrahydrothiazolo[3,4-b]isoquinoline-3-thione of the formula:

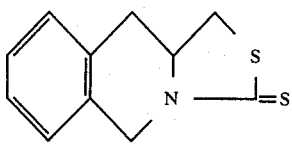

XIV

The reaction is generally carried out in an organic solvent or in a mixture of organic solvents, such as a mixture of toluene and tetrahydrofuran, at a temperature between 0° and 70° C.

The salts of general formula XIII wherein $R_2$ represents an alkylthio or benzylthio radical and $A^{\ominus}$ represents an iodide, sulphate, tetrafluoroborate or fluorosulphonate ion, can be obtained by the action of a reactive ester of the general formula:

$$R_3—A_1 \qquad XV$$

(wherein $R_3$ represents an alkyl radical containing 1 to 4 carbon atoms or a benzyl radical, and $A_1$ represents the residue of a reactive ester such as an iodine atom or an alkoxysulphonyloxy radical), or by the action of triethyloxonium tetrafluoroborate or methyl fluorosulphonate, on the compound of formula XIV. The reaction is generally carried out, optionally in the presence of an organic solvent, such as methylene chloride, at a temperature of about 20° C.

The thiazoloisoquinoline derivative of formula XIV can be prepared by reacting carbon disulphide in a basic medium with a 1,2,3,4-tetrahydroisoquinoline of the general formula:

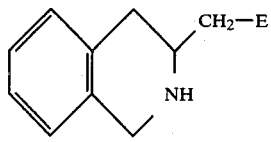

XVI wherein E represents a halogen, e.g. bromine or chlorine, atom or a hydroxysulphonyloxy radical. The reaction is generally carried out in an aqueous medium in the presence of sodium hydroxide at a temperature of about 20° C.

The compounds of general formula XVI can be obtained by the action of an inorganic acid on 3-hydroxymethyl-1,2,3,4-tetrahydroisoquinoline.

The compound of general formula XVI wherein E represents the hydroxysulphonyloxy radical is generally prepared by treatment of 3-hydroxymethyl-1,2,3,4-tetrahydroisoquinoline with sulphuric acid in an aqueous medium at a temperature of about 100° C., or in an organic solvent (such as dimethylformamide) in the presence of dicyclohexylcarbodiimide at a temperature of about 20° C.

The compound of general formula XVI wherein E represents the bromine atom is generally prepared by treatment of the said 3-hydroxymethyl compound with aqueous hydrobromic acid (48% w/v) at the reflux temperature of the reaction mixture, and isolating the product of general formula XVI as its hydrobromide.

The compound of general formula XVI wherein E represents the chlorine atom is generally prepared by treatment of the said 3-hydroxymethyl compound with thionyl chloride in an organic solvent, such as chloroform, saturated with hydrogen chloride, at the reflux temperature of the reaction mixture, and isolating the product of general formula XVI as its hydrochloride.

The isoquinoline derivatives of general formula III may be converted by known methods into acid addition salts. (By the term "known methods" is meant methods heretofore used or described in the chemical literature). The acid addition salts may be obtained by reacting the isoquinoline derivatives with acids in appropriate solvents. As organic solvents there may be used alcohols, ketones, ethers or chlorinated hydrocarbons. The salt which is formed is precipitated, if necessary after concentration of the solution, and is isolated by filtration or decantation.

The isoquinoline derivatives of general formula III and/or their acid addition salts can optionally be purified by physical methods such as crystallisation or chromatography.

The isoquinoline derivatives of general formula III possess useful pharmacological properties. They are particularly useful as analgesic, antiinflammatory and antipyretic agents.

Furthermore, the isoquinoline derivatives of general formula III in the (S) form, pure or mixed with a substantial proportion of the (R) form, are antiviral agents.

The anti-inflammatory activity of the isoquinoline derivatives manifests itself in rats at doses of between 5 and 50 mg/kg animal body weight, administered orally, using the technique of K. F. Benitz and L. M. Hall, Arch. Int. Pharmacodyn., 144, 185 (1963).

The analgesic activity manifests itself in rats at doses of between 2 and 30 mg/kg animal body weight administered orally, using the technique of E. Siegmund et al., Proc. Soc. Exp. Biol. Med., 95, 729 (1957), and using the technique of L. O. Randall and J. J. Selitto, Arch. Int. Pharmacodyn., 111, 409 (1957), modified by K. F. Swingle et al., Proc. Soc. Exp. Biol. Med., 137, 536 (1971).

The antipyretic acitivty manifests itself in rats at doses of between 2 and 30 mg/kg animal body weight, administered orally, using the technique of J. J. Loux et al., Toxicol. Appl. Pharmacol., 22, 674 (1972).

The antiviral activity manifests itself, in particular, against viruses of the rhinovirus group.

On cell cultures of human MRC-5 fibroblasts, infected with human type 1B rhinovirus (R 1112 strain), the isoquinoline derivatives of the present invention cause the complete inhibition of the cytopathogenic effect and of the multiplication of the viruses at concentrations of between about 7 μg/cc (maximum non-cytotoxic concentration) and 0.2 to 7 μg/cc (minimum inhibitory concentration).

Furthermore, the acute toxicity of the isoquinoline derivatives according to the invention, expressed as their $LD_{50}$, is more than 900 mg/kg animal body weight administered orally to mice.

Preferred isoquinoline derivatives of the present invention are those compounds of the general formula:

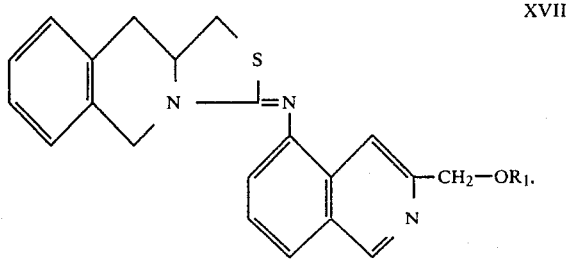

XVII wherein $R_1$, represents a straight- or branched-chain alkyl radical containing 1 to 4 carbon atoms, and more particularly 3-[(3-ethoxymethylisoquinol-5-yl)imino]-1,5,10,10a-tetrahydrothiazolo[3,4-b]isoquinoline and 3-[(3-methoxymethylisoquinol-5-yl)imino]-1,5,10,10a-tetrahydrothiazolo[3,4-b]isoquinoline, and their acid addition salts. Preferably the compounds are in the (S) form.

For therapeutic purposes the isoquinoline derivatives of general formula III are employed as such or in the form of pharmaceutically acceptable acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllineacetates, salicylates, phenolphthalinates and methylene-bis-$\beta$-hydroxynaphthoates) so that the beneficial physiological properties inherent in the bases are not vitiated by side-effects ascribable to the anions.

The following Examples illustrate the preparation of the new isoquinoline derivatives of the present invention.

EXAMPLE 1

(S)-3-Methylthio-1,5,10,10a-tetrahydrothiazolo[3,4-b]isoquinolinium iodide (7.2 g) is added to a solution of 5-amino-3-ethoxymethylisoquinoline (4.1 g) in pyridine (150 cc). The suspension is stirred for 24 hours at a temperature of about 20° C. The insoluble material gradually dissolves. The solution is concentrated to dryness under reduced pressure (20 mm Hg; 2.7 kPa) at 60° C. The residue is dissolved in a mixture of methylene chloride (100 cc) and N sodium hydroxide solution (100 cc). The organic phase is decanted, washed with water (50 cc), dried over magnesium sulphate and filtered and the filtrate is evaporated to dryness at 40° C. under reduced pressure (20 mm Hg; 2.7 kPa). The residue is recrystallised from isopropyl alcohol (80 cc). (S)-3-[(3-Ethoxymethylisoquinol-5-yl)imino]-1,5,10,10a-tetrahydrothiazolo[3,4-b]isoquinoline (5.2 g) is thus obtained in the form of a pale yellow solid melting at 88° C.

5-Amino-3-ethoxymethylisoquinoline can be prepared in the following manner:

A catalyst (3% palladium-on-charcoal; 3.5 g) is added to a solution of 3-ethoxymethyl-5-nitroisoquinoline (24 g) in ethanol (350 cc). A stream of hydrogen is bubbled through for 4 hours, whilst keeping the temperature at about 25° C. with the aid of a bath of cold water. The suspension is filtered and the filtrate is evaporated to dryness at 50° C. under reduced pressure (20 mm Hg; 2.7 kPa). The residue is recrystallized from diisopropyl ether (200 cc). 5-Amino-3-ethoxymethylisoquinoline (16.5 g), melting at 95° C., is obtained.

3-Ethoxymethyl-5-nitroisoquinoline can be prepared in the following manner:

3-Ethoxymethylisoquinoline (31 g) is dissolved in 95% sulphuric acid (density 1.83; 100 cc). The solution is cooled to 0° C. and a mixture of 95% sulphuric acid (density 1.83; 35 cc) and 70% nitric acid (density 1.42; 10.2 cc) is added dropwise in the course of 30 minutes so as not to exceed 10° C. Stirring is continued for 16 hours, whilst allowing the temperature to return to about 20° C. The mixture is then poured into a mixture of ice and water (1 liter), and an ammonia solution containing 20% of $NH_3$ (density 0.9) is added, without exceeding 30° C., until a pH of about 10 is obtained. The yellow suspension is extracted with methylene chloride (4×200 cc). The organic extracts are combined, washed with water (2×50 cc), dried over magnesium sulphate and filtered and the filtrate is evaporated to dryness at 40° C. under reduced pressure (20 mm Hg; 2.7 kPa). 3-Ethoxymethyl-5-nitroisoquinoline (24 g), melting at 54° C., is obtained.

3-Ethoxymethylisoquinoline can be prepared in the following manner:

A mixture of 3-chloromethylisoquinoline hydrochloride (40 g) and sodium ethoxide (40 g) in ethanol (700 cc) is heated under reflux for 8 hours. After cooling to 20° C., the mixture is filtered and the filtrate is evaporated to dryness at 50° C. under reduced pressure (20 mm Hg; 2.7 kPa). The residue is taken up in methylene chloride (500 cc), the mixture is washed with water (3×100 cc), the organic phase is dried over magnesium sulphate and filtered and the filtrate is evaporated to dryness at 40° C. under reduced pressure (20 mm Hg; 2.7 kPa). The oily residue is distilled at 110°–114° C. under a pressure of 0.6 mm Hg (0.08 kPa). 3-Ethoxymethylisoquinoline (31 g), which is a colourless oil, is obtained.

3-Chloromethylisoquinoline hydrochloride can be prepared in the following manner:

3-Hydroxymethylisoquinoline (110 g) is added to thionyl chloride (130 cc), whilst cooling so as to keep the temperature between 25° C. and 30° C. The reaction mixture is then heated to the reflux temperature at a rate which is such that the evolution of gas is not excessive. The mixture is heated under reflux for 90 minutes (until the evolution of gas ceases) and then for a further 30 minutes. It is cooled to 5° C. with ice, the slurry formed is filtered and the solid is washed with diethyl ether. 3-Chloromethylisoquinoline hydrochloride (136 g), melting at 202° C., is obtained.

3-Hydroxymethylisoquinoline can be prepared by the method described by B. R. Brown et al., J. Chem. Soc., 1145 (1951).

EXAMPLE 2

(S)-3-Benzylthio-1,5,10,10a-tetrahydrothiazolo[3,4-b]isoquinolinium iodide (0.06 g) is added to a solution of 5-amino-3-ethoxymethylisoquinoline (0.03 g) in pyridine (10 cc). The suspension is stirred for 48 hours at 20° C. The insoluble material gradually dissolves. The solution is then concentrated to dryness under reduced pressure (25 mm Hg; 3.3 kPa) at 60° C. The residue is dissolved in a mixture of methylene chloride (20 cc) and N sodium hydroxide solution (5 cc). After stirring and decantation, the organic phase is washed with water (2×10 cc), dried over sodium sulphate and filtered, and the filtrate is concentrated to dryness under reduced pressure (25 mm Hg; 3.3 kPa) at 40° C. (S)-3-[(3-Ethoxymethylisoquinol-5-yl)-imino]-1,5,10,10a-tetrahydrothiazolo[3,4-b]isoquinoline (0.04 g), m.p. 88° C., is obtained.

(S)-3-Benzylthio-1,5,10,10a-tetrahydrothiazolo[3,4-b]isoquinolinium iodide can be prepared in the following manner:

(S)-1,5,10,10a-Tetrahydrothiazolo[3,4-b]-isoquinoline-3-thione (8.8 g) is dissolved in methylene chloride (100 cc), and benzyl iodide (9.5 g) is added. After 48 hours at a temperature of about 20° C., diisopropyl ether (200 cc) is added. The resulting precipitate is filtered off, washed with diisopropyl ether and dried at 20° C. under reduced pressure (1 mm Hg; 0.13 kPa). (S)-3-Benzylthio-1,5,10,10a-tetrahydrothiazolo[3,4-b]isoquinolinium iodide (15.6 g) is thus obtained.

EXAMPLE 3

(S)-3-Methylthio-1,5,10,10a-tetrahydrothiazolo[3,4-b]isoquinolinium iodide (13.0 g) is added to a solution of 5-amino-3-methoxymethylisoquinoline (6.8 g) in pyridine (200 cc). After 18 hours at a temperature of about 20° C., the mixture is concentrated to dryness under reduced pressure (25 mm Hg; 3.3 kPa). The residue is dissolved in a mixture of 4 N sodium hydroxide solution (100 cc) and methylene chloride (200 cc). The organic phase is decanted, washed with water (100 cc), dried over magnesium sulphate and filtered, and the filtrate is then concentrated to dryness under reduced pressure (20 mm Hg; 2.7 kPa) at 40° C. The residue is crystallized by trituration with diisopropyl ether (50 cc) and then recrystallised from ethanol (200 cc). (S)-3-[(3-Methoxymethylisoquinol-5-yl)imino]-1,5,10,10a-tetrahydrothiazolo[3,4-b]isoquinoline (11.3 g) is thus obtained in the form of light beige crystals melting at 134° C.

$[\alpha]_D^{20} = -168° \pm 2°$ (c=1, chloroform).

5-Amino-3-methoxymethylisoquinoline can be prepared in the following manner:

A catalyst (3% palladium-on-charcoal; 8 g) is added to a solution of 3-methoxymethyl-5-nitroisoquinoline (78 g) in ethanol (2 liters). The resulting suspension is stirred and hydrogen is bubbled through for 6 hours, whilst keeping the temperature between 20° and 25° C. with the aid of a bath of cold water. The mixture is then filtered and the filtrate is evaporated to dryness at 60° C. under reduced pressure (20 mm Hg; 2.7 kPa). The residue is recrystallised from diisopropyl ether (500 cc). 5-Amino-3-methoxymethylisoquinoline (47 g), m.p. 105° C., is obtained.

3-Methoxymethyl-5-nitroisoquinoline can be prepared in the following manner:

3-Methoxymethylisoquinoline (68.8 g) is dissolved in 95% sulphuric acid (density 1.83; 300 cc). The solution is cooled to 0° C. and a mixture of 70% nitric acid (density 1.42; 25 cc) and 95% sulphuric acid (density 1.83; 100 cc) is added dropwise in the course of 30 minutes so as not to exceed 10° C. Stirring is continued for 16 hours, whilst allowing the temperature to return to about 20° C. The mixture is then poured into a mixture of ice and water (2 liters), and an ammonia solution containing 20% of $NH_3$ (density 0.9) is added, without exceeding 30° C., until a pH of about 10 is obtained. The resulting yellow solution is extracted with methylene chloride (4×400 cc). The organic extracts are combined, washed with water (2×50 cc), dried over magnesium sulphate and filtered, and the filtrate is evaporated to dryness at 40° C. under reduced pressure (20 mm Hg; 2.7 kPa). 3-Methoxymethyl-5-nitroisoquinoline (78 g), m.p. 91° C., is obtained.

3-Methoxymethylisoquinoline can be prepared in the following manner:

A mixture of 3-chloromethylisoquinoline hyrochloride (96 g) and sodium methoxide (80 g) in methanol (1.5 liters) is heated under reflux for 8 hours. After cooling to 20° C., the mixture is filtered and the filtrate is evaporated to dryness at 50° C. under reduced pressure (20 mm Hg; 2.7 kPa). The residue is taken up in methylene chloride (1 liter), the mixture is washed with water (3×150 cc), the organic phase is dried over magnesium sulphate and filtered and the filtrate is evaporated to dryness at 40° C. under reduced pressure (20 mm Hg; 2.7 kPa).

The oily residue is distilled at 82° C. under reduced pressure (0.6 mm Hg; 0.08 kPa). 3-Methoxymethylisoquinoline (68 g), which is a colourless oil, is obtained.

The present invention includes within its scope pharmaceutical compositions comprising, as active ingredient, at least one of the compounds of general formula III, or a non-toxic acid addition salt thereof, in association with a pharmaceutically acceptable carrier or adjuvant. The invention includes especially such preparations made up for oral, parenteral, intranasal, rectal or topical administration.

Solid compositions for oral administration include tablets, pills, powders and granules. In such solid compositions the active compound is admixed with at least one inert diluent such as sucrose, lactose or starch. The compositions may also comprise, as in normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as liquid paraffin. Besides inert diluents such compositions may also comprise adjuvants, such as wetting, emulsifying and suspending agents, and sweetening, flavouring and aromatizing agents. The compositions according to the invention for oral administration also include capsules of absorbable material such as gelatin containing the active substance with or without the addition of diluents or excipients, e.g. as powders.

Preparations according to the invention for parenteral administration include sterile non-aqueous solutions, suspensions or emulsions. Examples of non-aqueous solvents or vehicles are propylene glycol, polyethylene glycol, vegetable oils (in particular olive oil, sweet-almond oil or coconut oil), and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, by heating, or by the addition of a preservative. They may also be manufactured in the form of sterile solid compositions which can be dissolved in a sterile injectable medium immediately before use.

Compositions for rectal administration are suppositories which contain, in addition to the active substance, excipients such as cacao butter or a suitable wax base.

Compositions for topical aldministration can be, for example, in the form of ointments.

The percentage of active ingredient in the compositions of the invention may be varied, it being necessary that it should constitute a proportion such that a suitable dosage shall be obtained.

The compositions according to the invention are particularly useful in human therapy by virtue of their anti-inflammatory, analgesic and antipyretic effects and, if appropriate, antiviral action. They are indicated, in particular, for the treatment of viral infections of the respiratory tract and, if appropriate, for the treatment of inflammatory diseases (ankylosing spondylarthritis, acute articular rheumatism and arthrosis), acute and chronic pains, rheumatic and traumatic algias, dental, neurological and visceral pain, various algias (pain experienced by cancer patients) and febrile conditions.

In human therapy, the doses of the isoquinoline derivative(s) depend on the desired effect and the duration of the treatment. For an adult, they are generally between 100 and 2000 mg per day, administered orally. They can reach 100 mg per day when administered nasally (drops or sprays).

In general, the physician will decide the posology considered appropriate, taking into account the age, weight and other factors peculiar to the patient being treated.

The following Example illustrates pharmacological compositions according to the invention.

EXAMPLE 4

Tablets containing a 100 mg dose of active product and having the following composition are prepared in accordance with the usual technique:

| | |
|---|---|
| (S)-3-[(3-ethoxymethylisoquinol-5-yl)-imino]-1,5,10,10a-tetrahydrothiazolo-[3,4-b]isoquinoline | 0.100 g |
| starch | 0.110 g |
| precipitated silica | 0.035 g |
| magnesium stearate | 0.005 g |

EXAMPLE 5

Tablets weighing 0.400 g and containing a 0.200 g dose of active product and having the following composition are prepared:

| | |
|---|---|
| (S)-3-[(3-methoxymethylisoquinol-5-yl)imino]-1,5,10,10a-tetrahydrothiazolo[3,4-b]isoquinoline | 0.200 g |
| wheat starch | 0.137 g |
| dicalcium phosphate | 0.040 g |
| sodium salt of carboxymethylstarch | 0.015 g |
| magnesium stearate | 0.008 g |

The active product, the dicalcium phosphate and about 90% of the starch are mixed and sifted (mesh openings: 0.5 mm). The remainder of the starch (10%) is made into a paste, mixed with the sieved ingredients, granulated by means of a sieve (mesh openings: 0.8 mm), and dried in an oven at about 50° C. The sodium salt of carboxymethylstarch and the magnesium stearate are then added and the resulting mix is tabletted.

EXAMPLE 6

A 1% oily solution of active product for nasal administration is prepared by dissolving (S)-3-[(3-ethoxymethylisoquinol-5-yl)imino]-1,5,10,10a-tetrahydrothiazolo[3,4-b]isoquinoline (1 g) in olive oil (100 cc) at 40° to 50° C., and filtering the solution obtained through a Millipore filter.

For administration, the solution is applied to the nasal mucous membrane by means of a dropper.

We claim:

1. An isoquinoline derivative of the formula:

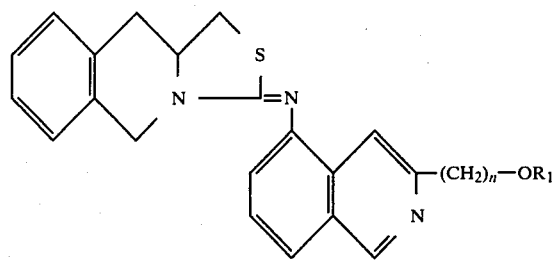

wherein $R_1$ represents alkyl of 1 through 8 carbon atoms and n represents 1 or 2, or a non-toxic pharmaceutically acceptable acid addition salt thereof.

2. An isoquinoline derivative according to claim 1 wherein $R_1$ represents alkyl of 1 through 4 carbon atoms and n represents 1, or a non-toxic pharmaceutically acceptable acid addition salt thereof.

3. An isoquinoline derivative according to claim 1 which is 3-[(3-ethoxymethylisoquinol-5-yl)imino]-1,5,10,10a-tetrahydrothiazolo[3,4-b]-isoquinoline or a non-toxic pharmaceutically acceptable acid addition salt thereof.

4. An isoquinoline derivative according to claim 1 which is 3-[(3-methoxymethylisoquinol-5-yl)imino]-1,5,10,10a-tetrahydrothiazolo[3,4-b]isoquinoline or a non-toxic pharmaceutically acceptable acid addition salt thereof.

5. An isoquinoline derivative according to claim 1, 2, 3 or 4 in the (S)-configuration.

6. A pharmaceutical composition useful as an analgesic, anti-inflammatory or antipyretic which comprises as active ingredient an effective amount of an isoquinoline derivative as claimed in claim 1, or a non-toxic pharmaceutically acceptable acid addition salt thereof, in association with a significant amount of a pharmaceutically acceptable carrier.

7. A pharmaceutical composition useful for the treatment of viral infections which comprises as active ingredient an effective amount of an isoquinoline derivative as claimed in claim 1 in the (S) form, or a non-toxic pharmaceutically acceptable acid addition salt thereof, in association with a significant amount of a pharmaceutically acceptable carrier.

* * * * *